United States Patent [19]

Foster et al.

[11] Patent Number: 5,680,661
[45] Date of Patent: Oct. 28, 1997

[54] HOSPITAL BED WITH USER CARE APPARATUS

[75] Inventors: L. Dale Foster; Ryan Anthony Reeder, both of Brookville; Allen L. Walke, Batesville; David W. Hornbach, Brookville, all of Ind.

[73] Assignee: Hill-Rom, Inc., Batesville, Ind.

[21] Appl. No.: 509,756

[22] Filed: Aug. 3, 1995

Related U.S. Application Data

[63] Continuation-in-part of Ser. No. 277,243, Jul. 19, 1994, Pat. No. 5,577,279, which is a continuation-in-part of Ser. No. 234,403, Apr. 28, 1994, Pat. No. 5,454,126, which is a continuation-in-part of Ser. No. 186,657, Jan. 25, 1994, and Ser. No. 230,061, Apr. 21, 1994, Pat. No. 5,513,406, which is a continuation-in-part of Ser. No. 186,657, Jan. 25, 1994, Ser. No. 221,748, Mar. 31, 1994, Ser. No. 221,633, Apr. 1, 1994, Pat. No. 5,483,709, and Ser. No. 7,122, Jan. 21, 1993, Pat. No. 5,337,845, which is a continuation-in-part of Ser. No. 912,826, Jul. 13, 1992, Pat. No. 5,335,651, which is a continuation-in-part of Ser. No. 874,586, Apr. 24, 1992, Pat. No. 5,370,111, which is a continuation-in-part of Ser. No. 524,038, May 16, 1990, Pat. No. 5,117,521.

[51] Int. Cl.⁶ .................................................. A61G 7/00
[52] U.S. Cl. ......................... 5/618; 5/620; 5/604; 5/613
[58] Field of Search ............................... 4/465, 480, 483, 4/600, 602, 604, 613, 617, 618, 620, 624

[56] References Cited

U.S. PATENT DOCUMENTS

| | | |
|---|---|---|
| D. 260,816 | 9/1981 | Zissimopoulos . |
| 1,290,809 | 1/1919 | Truax . |
| 1,398,203 | 11/1921 | Schmidt . |
| 1,992,262 | 2/1935 | Upp . |
| 2,039,901 | 5/1936 | Hawley . |
| 2,308,592 | 1/1943 | Drexler et al. . |
| 2,470,524 | 5/1949 | Scudder . |
| 2,607,929 | 8/1952 | Balluff . |
| 2,673,771 | 3/1954 | Krewson . |
| 2,696,963 | 12/1954 | Shepherd . |
| 2,847,006 | 8/1958 | Griffith . |
| 2,978,053 | 4/1961 | Schmidt . |
| 3,032,059 | 5/1962 | McLeod . |
| 3,038,174 | 6/1962 | Brown et al. . |
| 3,210,779 | 10/1965 | Herbold . |
| 3,281,103 | 10/1966 | Kisling . |
| 3,281,141 | 10/1966 | Smiley et al. . |
| 3,524,512 | 8/1970 | Voeks et al. . |
| 3,593,350 | 7/1971 | Knight et al. . |
| 3,596,725 | 8/1971 | Homs . |
| 3,795,284 | 3/1974 | Mracek et al. . |
| 3,876,018 | 4/1975 | Mracek et al. . |
| 3,876,024 | 4/1975 | Shieman et al. . |
| 3,948,344 | 4/1976 | Johnson et al. . |
| 4,006,789 | 2/1977 | Stultz et al. . |
| 4,033,420 | 7/1977 | De Masters . |
| 4,139,917 | 2/1979 | Fenwick .......................... 5/602 |
| 4,155,421 | 5/1979 | Johnson et al. . |
| 4,225,104 | 9/1980 | Larson . |
| 4,225,989 | 10/1980 | Corbett et al. . |
| 4,227,269 | 10/1980 | Johnston . |
| 4,262,872 | 4/1981 | Kodet . |
| 4,272,856 | 6/1981 | Wegener et al. . |
| 4,281,730 | 8/1981 | Swersey et al. . |
| 4,298,083 | 11/1981 | Johnson et al. . |

(List continued on next page.)

FOREIGN PATENT DOCUMENTS

| | | |
|---|---|---|
| 2285113 | 4/1976 | France . |
| 2818189 | 6/1979 | Germany . |
| 2812037 | 9/1979 | Germany . |
| 3915882 | 11/1990 | Germany . |
| 2153771 | 8/1985 | United Kingdom . |

Primary Examiner—Michael F. Trette
Attorney, Agent, or Firm—Barnes & Thornburg

[57] ABSTRACT

A hospital bed that converts from a bed configuration to a chair configuration that is used in combination with different care/therapy modules. When in the chair configuration, the bed is designed to interface at its foot end with the different care/therapy modules to facilitate the use of such modules. The care/therapy modules include, for example, a general purpose cart, a motorized leg exercise device, a walking exercise device, a non-motorized leg exercise device, a commode, a wheelchair and/or a hydrotherapy unit.

10 Claims, 6 Drawing Sheets

U.S. PATENT DOCUMENTS

| | | |
|---|---|---|
| 4,352,991 | 10/1982 | Kaufman . |
| 4,356,578 | 11/1982 | Clark .......................................... 5/600 |
| 4,399,885 | 8/1983 | Johnson et al. . |
| 4,417,638 | 11/1983 | Harvey . |
| 4,417,639 | 11/1983 | Wegener . |
| 4,420,052 | 12/1983 | Hale . |
| 4,435,864 | 3/1984 | Callaway . |
| 4,482,783 | 11/1984 | Laimins . |
| 4,487,276 | 12/1984 | Swersey et al. . |
| 4,511,158 | 4/1985 | Varga et al. . |
| 4,517,690 | 5/1985 | Wegener . |
| 4,528,704 | 7/1985 | Wegener et al. . |
| 4,567,957 | 2/1986 | Johnson . |
| 4,578,833 | 4/1986 | Vrzalik . |
| 4,584,989 | 4/1986 | Stith . |
| 4,592,104 | 6/1986 | Foster . |
| 4,600,209 | 7/1986 | Kerr . |
| 4,627,426 | 12/1986 | Wegener et al. . |
| 4,639,954 | 2/1987 | Speed . |
| 4,686,719 | 8/1987 | Johnson et al. . |
| 4,691,397 | 9/1987 | Netzer . |
| 4,729,576 | 3/1988 | Roach . |
| 4,768,241 | 9/1988 | Beney . |
| 4,793,428 | 12/1988 | Swersey . |
| 4,795,122 | 1/1989 | Petre . |
| 4,821,348 | 4/1989 | Pauna . |
| 4,862,529 | 9/1989 | Peck . |
| 4,894,876 | 1/1990 | Fenwick . |
| 4,896,389 | 1/1990 | Chamberland . |
| 4,905,944 | 3/1990 | Jost . |
| 4,920,587 | 5/1990 | Kerr . |
| 4,944,292 | 7/1990 | Gaeke . |
| 4,945,592 | 8/1990 | Sims . |
| 4,949,413 | 8/1990 | Goodwin . |
| 4,953,243 | 9/1990 | Birkmann . |
| 4,953,247 | 9/1990 | Hasty . |
| 4,957,121 | 9/1990 | Icenogle . |
| 4,962,552 | 10/1990 | Hasty . |
| 4,966,340 | 10/1990 | Hunter . |
| 4,985,946 | 1/1991 | Foster et al. . |
| 4,987,620 | 1/1991 | Sharon . |
| 5,005,230 | 4/1991 | Congdon . |
| 5,022,105 | 6/1991 | Catoe . |
| 5,033,563 | 7/1991 | Brainerd, Jr. et al. . |
| 5,042,470 | 8/1991 | Kanesaka . |
| 5,044,029 | 9/1991 | Vrzalik . |
| 5,050,695 | 9/1991 | Kleinwulterink . |
| 5,054,141 | 10/1991 | Foster et al. . |
| 5,065,464 | 11/1991 | Blanchard et al. . |
| 5,067,189 | 11/1991 | Weedling et al. . |
| 5,072,906 | 12/1991 | Foster . |
| 5,077,843 | 1/1992 | Foster et al. . |
| 5,083,331 | 1/1992 | Schnelle et al. . |
| 5,083,625 | 1/1992 | Bleicher . |
| 5,090,077 | 2/1992 | Caden et al. . |
| 5,092,007 | 3/1992 | Hasty . |
| 5,103,518 | 4/1992 | Gilroy et al. . |
| 5,103,519 | 4/1992 | Hasty . |
| 5,109,560 | 5/1992 | Uetake . |
| 5,117,521 | 6/1992 | Foster et al. . |
| 5,117,819 | 6/1992 | Servidio . |
| 5,121,512 | 6/1992 | Kaufmann . |
| 5,157,800 | 10/1992 | Borders . |
| 5,181,289 | 1/1993 | Kassai . |
| 5,193,633 | 3/1993 | Ezenwa . |
| 5,335,651 | 8/1994 | Foster et al. . |
| 5,337,845 | 8/1994 | Foster et al. . |
| 5,370,111 | 12/1994 | Reeder et al. . |
| 5,398,357 | 3/1995 | Foster . |
| 5,513,406 | 5/1996 | Foster et al. ................................. 5/600 |
| 5,535,459 | 7/1996 | DiMatteo et al. ...................... 5/600 X |

HOSPITAL BED WITH USER CARE APPARATUS

RELATED APPLICATIONS

This application is a continuation-in-part of application Ser. No. 08/277,243, filed Jul. 19, 1994, entitled HOSPITAL BED, now Pat. No. 5,577,279 which is a continuation-in-part of application Ser. No. 08/234,403, filed Apr. 28, 1994, entitled FOOT EGRESS CHAIR BED, now Pat. No. 5,454,126 which is a continuation-in-part of application Ser. No. 08/186,657, filed Jan. 25, 1994, entitled FOOT EGRESS CHAIR BED, still pending and a continuation-in-part of application Ser. No. 08/230,061, filed Apr. 21, 1994, entitled MODULAR HOSPITAL BED AND METHOD OF PATIENT HANDLING, now Pat. No. 5,513,406, which is a continuation-in-part of application Ser. No. 08/186,657, filed Jan. 25, 1994, entitled FOOT EGRESS CHAIR BED, still pending, a continuation-in-part of application Ser. No. 08/221,748, filed Mar. 31, 1994, entitled USER WEIGH SCALE, still pending, a continuation-in-part of application Ser. No. 08/221,633, filed Apr. 1, 1994, entitled LOW AIR LOSS MATTRESS WITH RIGID INTERNAL BLADDER AND AIR PALLET, now Pat. No. 5,483,709, and a continuation-in-part of application Ser. No. 08/007,122, filed Jan. 21, 1993, entitled VENTILATOR, CARE CART AND MOTORIZED TRANSPORT EACH CAPABLE OF NESTING WITHIN AND DOCKING WITH A HOSPITAL BED BASE, now Pat. No. 5,337,845, which is a continuation-in-part of application Ser. No. 07/912,826, filed Jul. 13, 1992, entitled VENTILATOR AND CARE CART EACH CAPABLE OF NESTING WITHIN AND DOCKING WITH A HOSPITAL BED BASE, now Pat. No. 5,335,651, which is a continuation-in-part of application Ser. No. 07/874/586, filed Apr. 24, 1992, entitled MOBILE VENTILATOR CAPABLE OF NESTING WITHIN AND DOCKING WITH A HOSPITAL BED BASE, now Pat. No. 5,370,111, which is a continuation-in-part of application Ser. No. 07/524,038, filed May 16, 1990, now U.S. Pat. No. 5,117,521, entitled CARE CART AND TRANSPORT SYSTEM, all of which are hereby incorporated by reference herein as if fully set forth in their entirety.

FIELD OF THE INVENTION

This invention relates generally to hospital beds, and more particularly to a combination of a hospital bed that converts from a bed configuration to a chair configuration in combination with different user care modules.

BACKGROUND OF THE INVENTION

During the period of time that a user is confined to a hospital bed, it is generally necessary that the user leave the bed to engage in user care or therapeutic activities, for example, to move to a wheelchair, to use a commode or toilet, to simply sit in a chair, to perform physical therapy, etc. When a weak user is removed from a traditional hospital bed, at least one and sometimes two attendants are required to stabilize, hold and often lift the user from the bed. Further, the process of sitting up and twisting around to obtain access to the side of the bed contorts the user and often induces pain especially, in users in a post-surgical situation. In addition, there are minimal handles and supports that are readily accessible to the user to assist and help in the process. Therefore, traditional beds and techniques have the disadvantages of making the seemingly simple process of getting out of a hospital bed physically difficult, labor intensive and often painful.

To provide more self sufficiency and to facilitate the process of a user leaving a bed, a hospital bed has been developed which automatically converts from a bed configuration to a chair configuration. Such a hospital bed is disclosed in co-pending applications Ser. Nos. 08/277,243 08/234,403 and 08/186,657 assigned to the assignee of the present invention. In those applications, chair beds are disclosed which have vacatable foot sections which, when the user support platform is lowered to a lowermost position, allow the user's feet to rest directly on the floor. Pivoting footboard halves convert into side guards/handrails that extend longitudinally from the foot end of the bed. The handrails may be grasped by the user to provide stabilization and support in moving from a sitting position to a standing position and in leaving the chair configured bed. Further, the user can also selectively raise and lower the bed to facilitate moving either from a seated to a standing position, or, from a standing to a seated position, respectively.

Further, the above described hospital bed permits a new method of user handling and care as disclosed in co-pending application Ser. No. 08/230,061 also assigned to the assignee of the present invention, in which a single hospital bed replaces the up to three prior hospital beds of traditional and different designs. Further, the method provides for the docking of different user care modules to the hospital bed during different user care stages.

SUMMARY OF THE INVENTION

An object of the present invention is to provide a hospital bed in combination with different user care modules that provides an environment accommodating user weaknesses and disabilities and that raises the level of physical security for a user in the process of moving from the hospital bed to different ones of the user care modules.

Another object of the invention is to provide a hospital bed in combination with different user care modules that provides guidance and support for a user in the process of moving from the hospital bed to another user care module, thereby reducing user fear and enhancing user confidence.

A further object of the invention is to provide a hospital bed in combination with different user care modules that provides a higher level of user independence and self sufficiency, thereby encouraging a user to engage in physical activity and therapy to reduce muscular atrophy and increase a user's sense of wellness.

To overcome the disadvantages of traditional hospital equipment, the present invention provides a combination of a hospital bed that moves from a bed position to a chair position and different user care modules located at the foot end of the bed so that a user may interface with the user care modules with a high level of security and confidence.

According to the principles of the present invention and in accordance with the described embodiments, a bed includes a base having a head end and a foot end. A support platform is mounted on the base and is selectively moveable between a generally planar bed position and a chair position. The support platform includes a head panel that moves to a raised position when moving the support platform to the chair position. The support platform further includes leg and foot panels that move relative to each other and the head panel to a position that allows the patient to leave the bed at the foot end of the base and frame assembly. A care/therapy module is removably coupled to the foot end of the base and frame assembly. The care/therapy module may be a general purpose cart, a motorized leg exercise device, a walking exercise device, a non-motorized leg exercise device, a commode, a wheelchair and/or a hydrotherapy unit. These and other objects and advantages of the present invention will become more readily apparent during the following detailed description together with the drawings herein.

BRIEF DESCRIPTION OF THE DRAWINGS

The several features of the invention will become more readily apparent from the following detailed description taken in conjunction with the accompanying drawings in which.

DETAILED DESCRIPTION OF THE INVENTION

Figure 1:
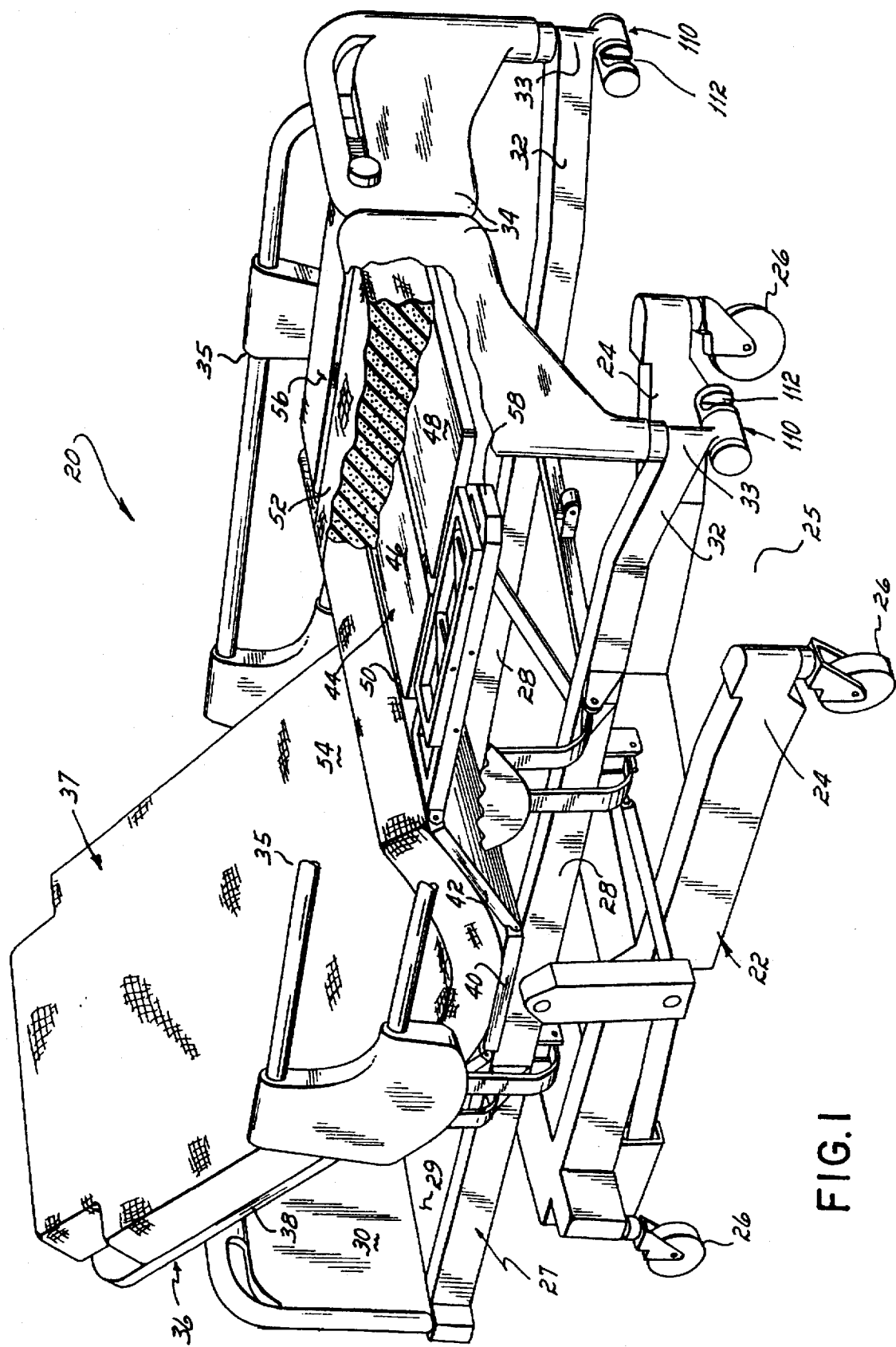
FIG. 1 is a perspective view of a hospital bed in accordance with the principles of the present invention.

Referring to FIG. 1, a modular bed 20 according to the principles of the invention includes a base 22 having a longitudinally oriented stem (not shown), a pair of outspread diverging arms 24 on one end thereof forming a foot end cavity 25 between the diverging arms 24. Casters 26 are mounted at the rear corners of the base 22 and to the ends of the outspread arms 24. The bed 20 further includes a mainframe 27 and linkage (not shown) mounting the mainframe 27 above the base 22, thereby permitting the mainframe 27 to be selectively raised and lowered in the vertical direction with respect to the base 22. The mainframe 27 includes a pair of longitudinally oriented rails or frame members 28 which span the length of the bed 20. Connected to the head end of each of the rails 28 is a transverse cross member 29 from which a head board 30 extends upwardly. At the foot end of the mainframe 27, each of the rails 28 includes a laterally outwardly diverging section 32.

Figure 2:
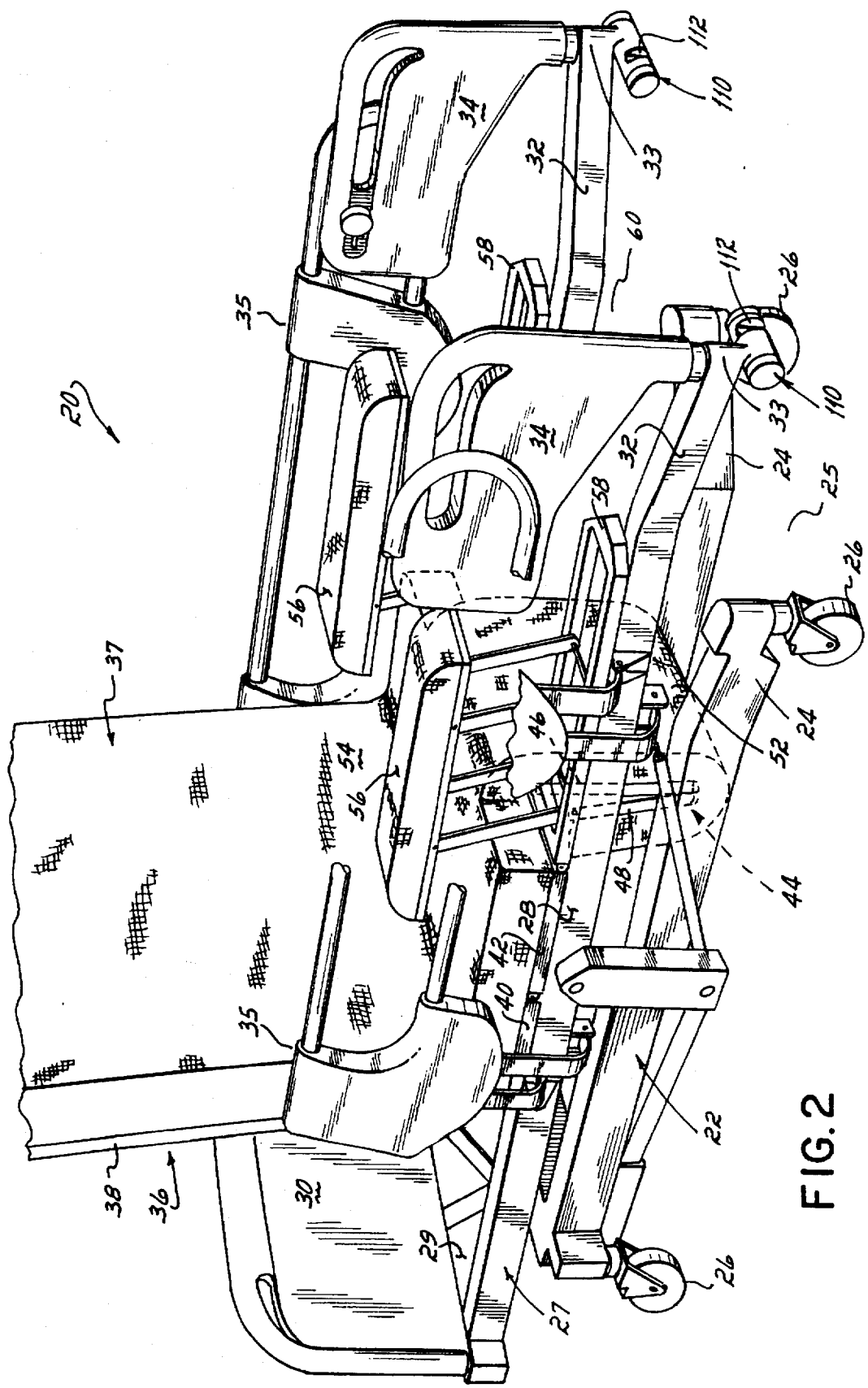
FIG. 2 is a perspective view of the hospital bed in a chair configuration.

Pivotally attached to the ends 33 of the sections 32 are pivoting footboard halves 34. The pivoting footboard halves or footgates 34 when oriented generally colinear with each other at the foot end of the bed 20 function together as a footboard for protection of the user when the bed 20 is in the bed configuration of FIG. 1. Each of the footboard halves 34 can be pivoted approximately 90° toward the head end of the bed, so that they extend along the lateral sides of the bed 20 and are generally parallel with each other. When in this position, the footboard halves 34 function separately as side guards/handrails for aiding a patient in egressing from the bed when the bed is configured as a chair (FIG. 2). The bed 20 further includes user guards 35 which are connected to the mainframe 27 and are mounted about a user support platform 36.

The user support platform 36 has a multiple component overlying mattress 37 on which a user is situated, and at least a portion of which is preferably inflated. The user support platform 36 can be converted to and between the generally horizontal bed configuration of FIG. 1 and a chair configuration as shown in FIG. 2. The user support platform 36 is articulated and consists of a plurality of serially hinged platform sections, including a head panel 38, a seat panel 40, a thigh panel 42, and leg panel 44, which includes a calf supporting panel 46, and a foot supporting panel 48. The foot supporting panel 48 is pivotally connected at its head end to the foot end of the calf supporting panel 46 by hinges 50. The head end of the leg panel section 44 is similarly hinged to the seat panel 40. A mattress section 52 covers the leg panel 44 and includes a resilient foam section surrounded by a sheet made of a flexible material. A second mattress section 54 overlies the balance of the user support platform 36 and includes arms or bolsters 56 which overlie lateral portions 58 of the leg panel 44.

More particularly, in referring to FIG. 1, it will be seen that when in the bed position, the foot support panel 48 and calf support panel 46 generally lie within a common plane. In moving from the bed position of FIG. 1 to the chair position of FIG. 2, the user support platform 36 is translated longitudinally toward the head end of the bed. As the platform 36 rolls toward the head end of the bed 20, the head panel 38 pivots upwardly and the foot panel 48 moves approximately 90° to a generally vertically position. Continued longitudinal movement of the platform 36 causes the foot end of calf support 46 to pivot downwardly and the head end of calf support 46 to move upwardly. By virtue of its pivoted connection 50 to thigh panel 42, movement of the platform 36 causes calf panel 46 to be rotated approximately 90° downward to a generally vertical position; and the foot support 48 is moved approximately 180° with respect to the calf panel 46 and 270° with respect to its original position. Thus, in the chair position of FIG. 2, the foot panel 48 is positioned aft of the generally vertically calf panel 46, and is generally juxtaposed to or against the calf panel 46. Moving the bed 20 to the chair position of FIG. 2 forms a vacatable foot portion 60 within the user support platform 36 which together with the foot end cavity 25 of the base 22 permits the user to easily egress from the foot end of the bed 20.

In accordance with the principles of the present invention, many different user care/rehabilitation modules may be coupled to the foot end of the bed 20. Some of the modules require that the user move through the vacatable foot portion 60 and foot end cavity 25 to use the module. Other modules are designed to themselves substantially occupy the vacatable foot portion 60 and the foot end cavity 25. For example, referring to FIG. 3, a rollable general purpose cart module 90 extends substantially within the vacatable foot portion 60 and foot end cavity 25 and is dockable, that is, removably coupled or connected to the ends 33 of the arms 32 of the main frame 27. The general purpose cart 90 comprises a lower frame 92, an upper frame 94, a pair of vertical rear posts 96 connected between the lower and upper frames 92, 94, and a pair of vertical forward posts 98, also connected between the lower and upper frames 92, 94. A support frame structure 100 is slidably mounted on and between a forward cross member 102 and a rear cross member 104. The support frame structure 100 is slidable from side to side on the cross members 102, 104 between the side bars 106 of the upper frame 94.

Figure 4:
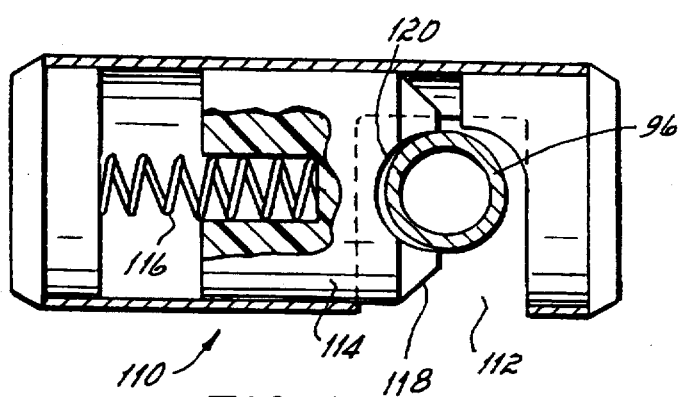
FIG. 4 is a view taken along line 4—4 of FIG. 3.

As shown in FIG. 4, latch blocks 110 are secured to the foot ends 33 of the arms 32 of frame 27. Each latch block 110 preferably has a tube with a notch 112 therein for accepting a respective vertical post 96. A plunger 114 is spring-loaded towards a closed position by a compression spring 116 within the latch block 110. The plunger 114 includes a chamfer 118 and a semi-circular groove 120. The chamfer 118 aids in compressing the plunger 114 and hence compression spring 116 by the rear vertical post 96. Once the vertical post 96 reaches the semi-circular notch 120, the plunger 114 snaps securely against the vertical rear post 96.

Figure 3:
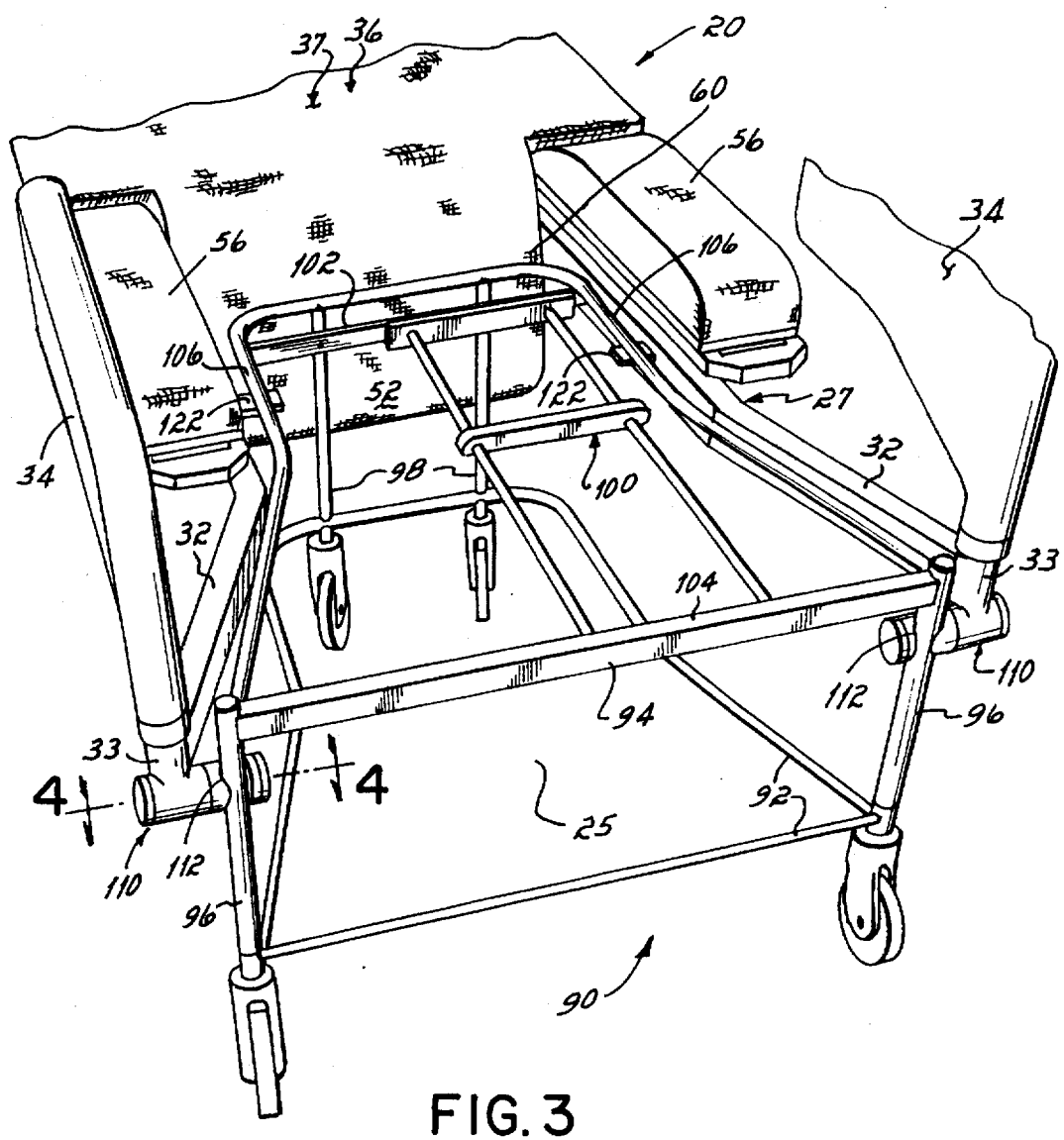
FIG. 3 is a partial perspective view of the hospital bed in combination with a general purpose cart connected thereto.

Support pads or plates, for example, ears 122 of FIG. 3 are connected to the lowermost side of the arms 32, and the ears 122 extend laterally and inwardly with respect to the frame 27. When the general purpose cart 90 is rolled into the vacating foot portion 60 and foot end cavity 25, the lateral side bars 106 of the upper frame 44 slide over the ears 122. Simultaneously, the rear post 96 engage the latch blocks 110 immediately below the rear cross member 104. Once the cart 90 is secured in place with respect to the frame 27, the cart 90 travels in the vertical direction with the frame 27 and the user support platform 36 as they are raised and lowered. The cart 90 is supported at its forward end by the ears 122 bearing underneath the forward upper bars 106. The cart 90 is supported in the rear by the uppermost surfaces of the latch blocks 110 bearing against a lower surface of the rear cross member 104.

Figure 5:
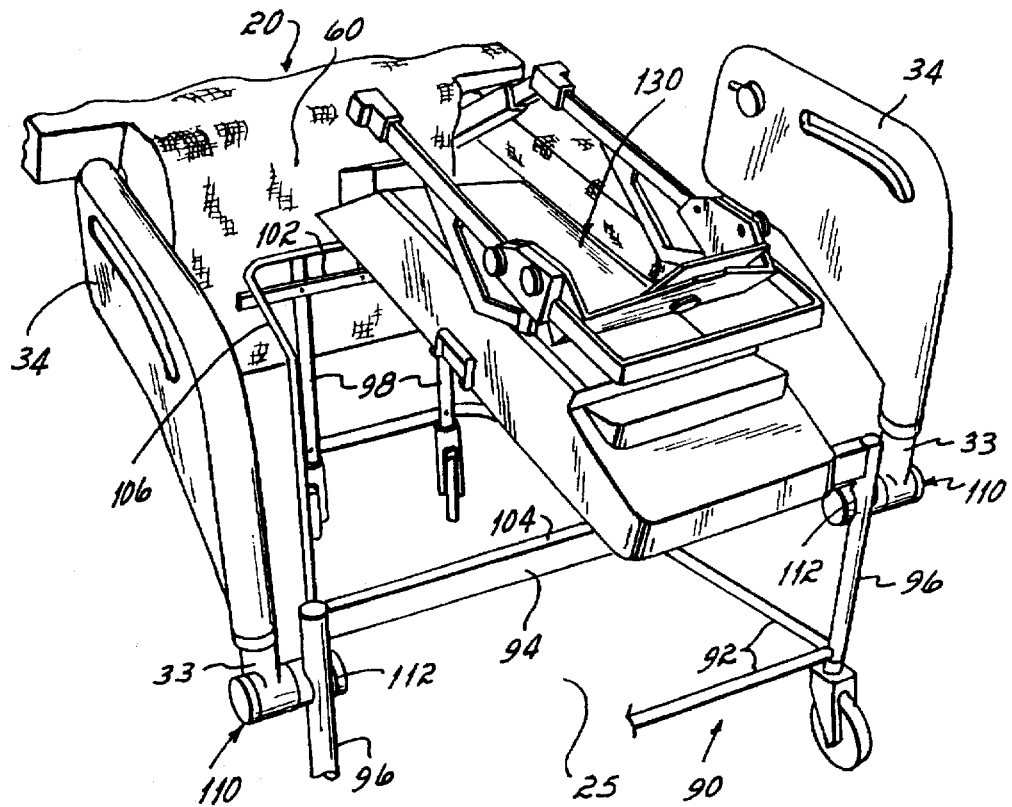
FIG. 5 is a partial perspective view of the hospital bed in combination with a cart containing a passive motion device.

The general purpose cart 90 may be designed such that the support frame 100 is slidable as described, lockable in a desired position, and manufactured to be at any desired elevation. Different therapeutic and user care appliances may be used in association with the cart module 90. For example, as illustrated in FIG. 5, a motorized passive motion device 130 may be mounted on the support frame 100. The passive motion device may be one of several such devices which are commercially available in which an electric motor moves a linkage that exercises the leg of a user independent of the user's muscular system. Typically, a passive motion device is placed on top of a mattress of the hospital bed and in such position is not at its optimum elevation. With the apparatus of FIG. 5, the cart 90 can be designed to present the passive motion device to the user at the preferred elevation and orientation with respect to the hospital bed and the user's posture.

Figure 6:
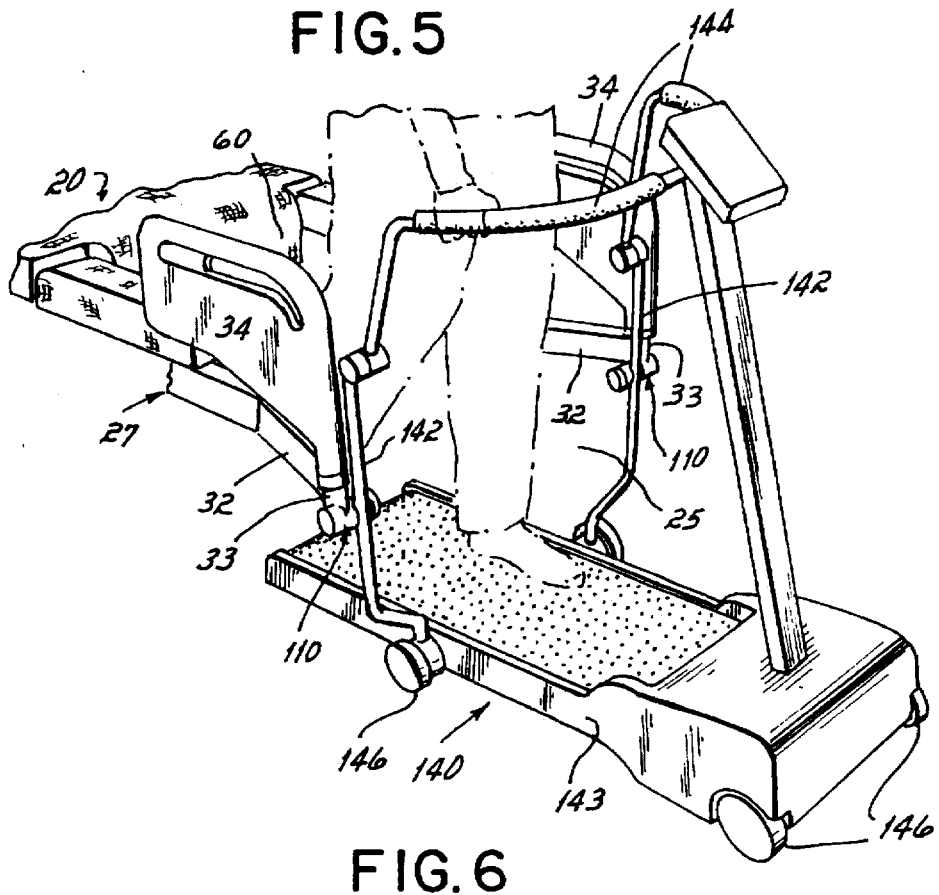
FIG. 6 is a partial perspective view of the hospital bed in combination with and connected to a treadmill.

FIG. 6 illustrates the combination of the hospital bed 20 and a treadmill 140. The treadmill 140 contains vertical posts 142 extending upward from a lower frame 143 that connect to the U-shaped handle bar 144 and couple into the latch blocks 110. The treadmill 140 has wheels 146 that permit it to be easily moved between locations. However, the coupling of the latch blocks 110 onto the vertical posts 142 secures the treadmill 140 to the bed 20 during its use by the user.

Figure 7:
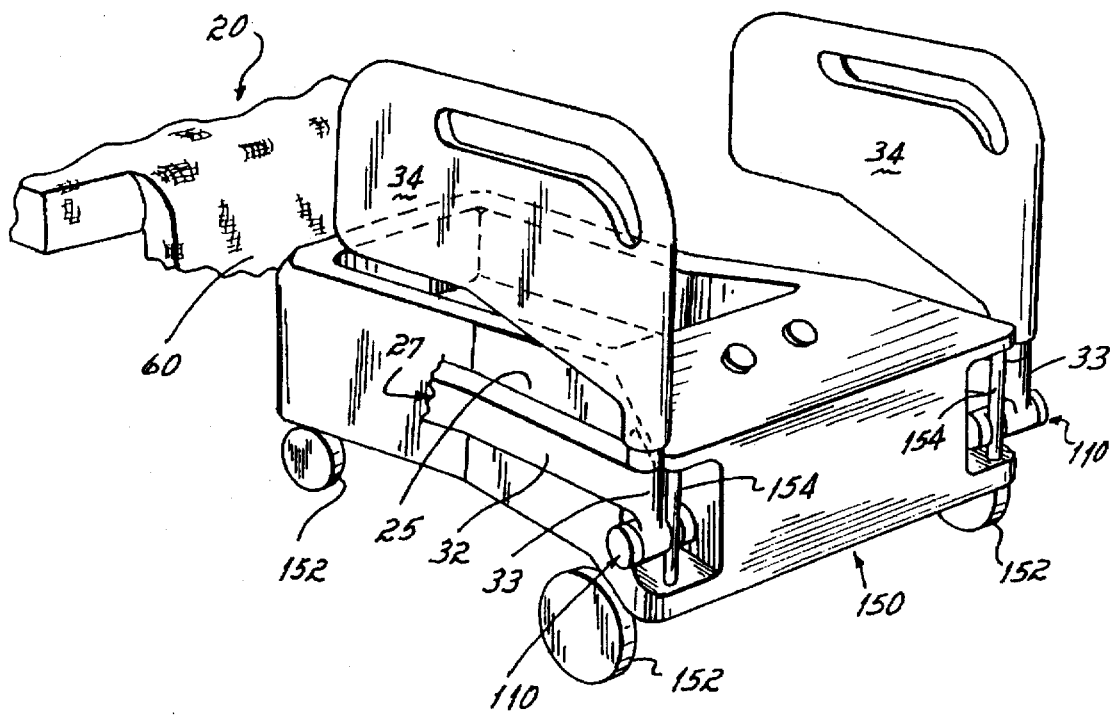
FIG. 7 is a partial perspective view of the hospital bed in combination with and connected to a water care/therapy unit.

Referring to FIG. 7, the bed 20 may be used in combination with a water care/therapy unit 150, for example, a hydrotherapy tub. The hydrotherapy tub 150 includes casters 152 which allow it to be easily moved into the foot end cavity 25 of the base (not shown in FIG. 7) and the vacatable foot portion 60 of the user support platform 36. The water care/therapy unit 150 includes vertical docking posts 154 at its rear corners which interlock with the latch blocks 110 thereby securing the unit 150 to the bed 20 and preventing it from moving away from the user during use.

Figure 8:
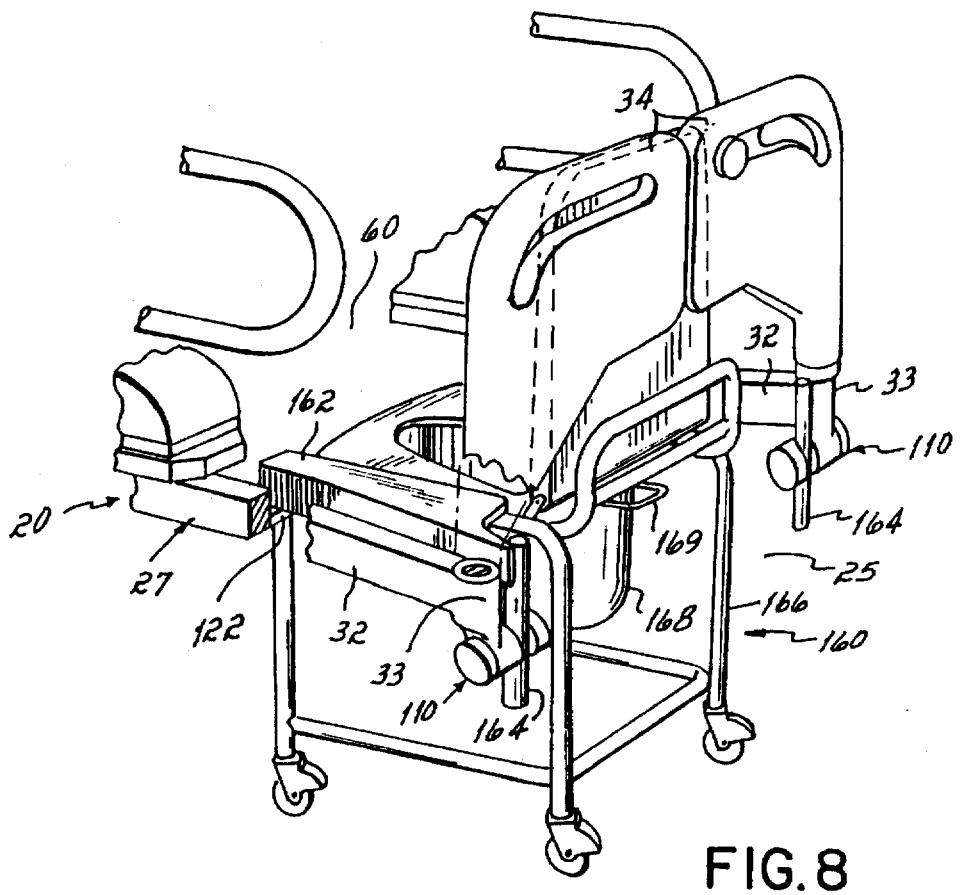
FIG. 8 is a partial perspective view of the hospital bed connected to and in combination with a portable commode module.

FIG. 8 illustrates the combination of a commode 160 with the bed 20. The commode 160 is more fully described in copending U.S. patent application Ser. No. 08/503,017 filed Jul. 17, 1995 entitled BEDSIDE CABINET FOR STORING APPLIANCES, now U.S. Pat. No. 5,662,396 and assigned to the Assignee of the present invention. The commode 160 has lateral frame members, for example, the wings 162 which are illustrated in their horizontal position. The wings 162 have, at their rearward corners, vertical docking posts 164 which interlock with the latch blocks 110, thereby securing the commode to the bed 20. The wings 162 also slide over and are supported by the ears 122 on the arms 32 of the frame 27; and therefore, the commode 160 is raised and lowered with the frame 27 to facilitate use by the user in the transition from the standing to the seated positions and vice versa. It should be noted that the commode 160 is designed to be stored within the bed 20; and for that purpose, the wings 162 are collapsible, that is, they fold downward to a generally vertical orientation. The commode 160 is more fully described in U.S. patent application Ser. No. 08/277,243 entitled HOSPITAL BED and assigned to the Assignee of the present invention. The frame 166 of the commode 160 has an unobstructed rear side so that the commode bowl 168 may be removed and installed from the commode 160 by moving the bowl 168 through the rear side of the frame 166. The commode bowl 168 has a handle 169 extending from the rear side of the bowl 168 to the rear side of the frame 166 to facilitate removal and insulation of the bowl 168.

Figure 9:
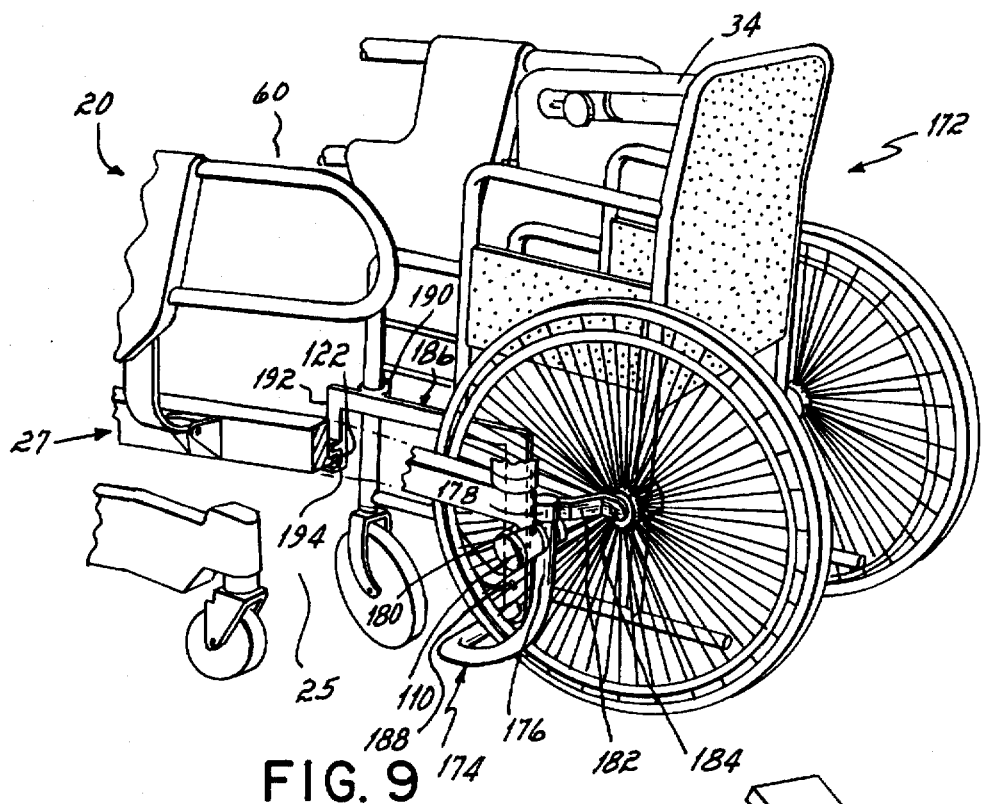
FIG. 9 is a partial perspective view of the hospital bed connected to and in combination with a wheelchair.

Referring to FIG. 9, the bed 20 may be used in combination with a wheelchair 172. The wheelchair 172 is a standard wheelchair that has a support device, for example, a pair of brackets 174 attached to and extending laterally from both sides of the wheelchair 172. The brackets 174 permit the wheelchair to be docked into and lifted by the mainframe 27 of the bed 20. Each of the brackets 174 includes a docking post 176 which preferably is made from stainless steel tubing. The docking posts 176 have vertically oriented upper ends that are terminated with aluminum caps 178. Each of the caps 178 is T-shaped with a cylindrical body section (not shown) that is inserted inside the end of the docking post 176 and held in place by a pin or other fastener (not shown). Each of the caps 178 further include a cylindrical top 180 which has a diameter greater than the diameter of the docking post 176. Plates 182 have first ends preferably welded or otherwise connected to the vertical ends of the docking posts 176, and opposite ends mounted on the ends of the axle 184 of the wheelchair 172. The docking posts 176 are generally L-shaped and have generally horizontal lower ends welded or otherwise rigidly connected to ends of inverted J-shaped brackets 186 which, in turn, are attached to the sides of the wheelchair 172. The inverted J-shaped brackets 186 are preferably made from flat rectangular bar stock and are connected at locations 188 and 190 to the frame of the wheelchair 172 by tubing straps or other fastening devices. The inverted J-shaped brackets 186 have shorter legs 192 that extend in a generally downward and have generally U-shaped or forked members 194. The coupling members 194 are oriented so that their open ends are directed laterally outward relative to the wheelchair 172.

As the wheelchair 172 is rolled into the foot cavity 25 of the bed 20, the docking posts 176 interconnect with the latching blocks 110; and the ears 122 are captured within the forked members 174. The legs of the forked members 194 overlap with the upper and lower surfaces of the ears 122. As the frame 27 is raised, the latching blocks 110 bear against the lower surfaces of the cylindrical tops 180 of the caps 178; and the ears 122 bear against the upper legs of the forked members 194, thereby lifting the wheelchair 172 with the frame 27. Raising and lowering the wheelchair 172 with the frame 27 assists the user in sitting on and rising from the wheelchair 172, as further described in U.S. patent application Ser. No. 08/277,243, filed on Jul. 19, 1994 and assigned to the Assignee of the present invention.

Figure 10:
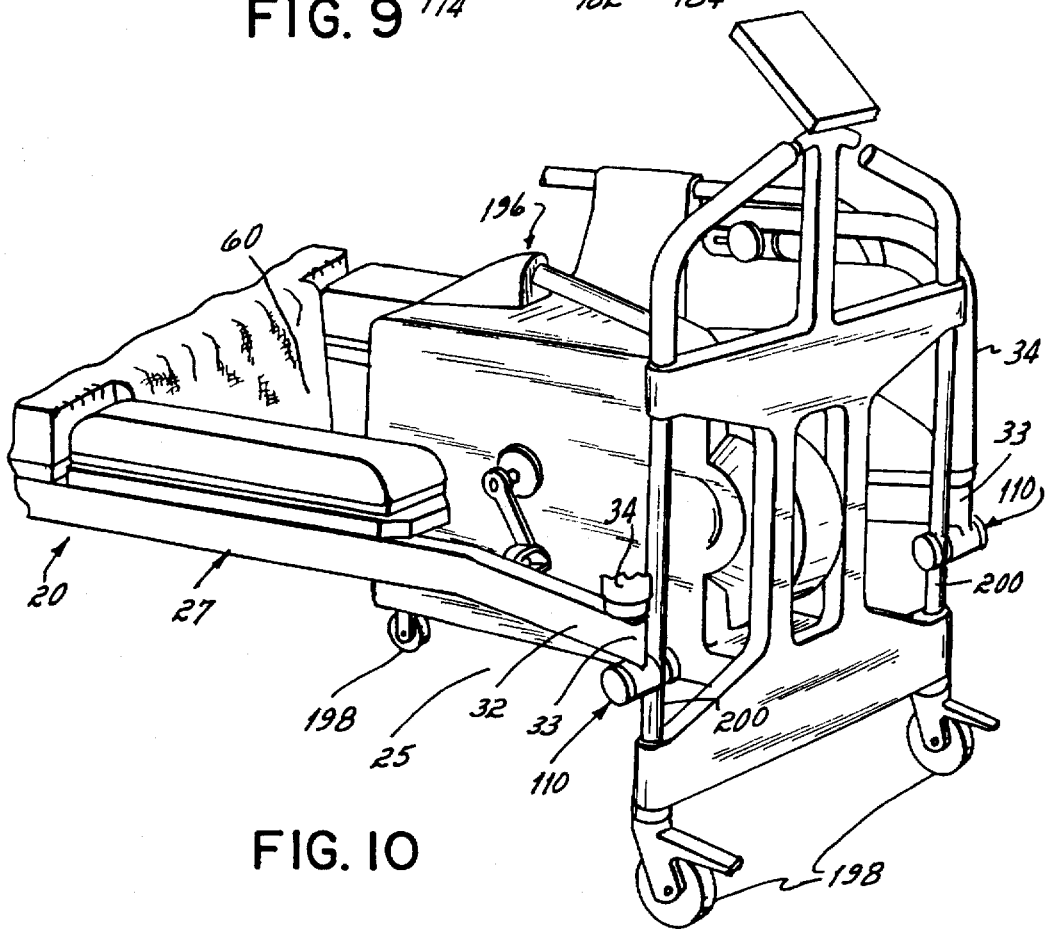
FIG. 10 is a partial perspective view of the hospital bed connected to and in combination with a leg exercise module.

FIG. 10 illustrates the combination of the bed 20 with a nonmotorized leg exercise device 196 which is mounted on casters 198 to facilitate moving it from location to location. The leg exercise device 196 is rolled into the contiguous foot end cavity 25 and vacatable foot cavity 60 until the latching blocks 110 interlock with vertical docking posts 200 when secured in that position, the leg exercise device 196 is prevented from moving away from the bed 20 when being used. Such a leg exercise device is further described in U.S. patent application Ser. No. 08/230,061 filed on Apr. 21, 1994 and assigned to the Assignee of the present invention.

In use, the hospital bed in accordance with the principles of the present invention is used with many different care/therapy modules to fill a wide range of user needs and thereby provide improved, comprehensive care. The combination of the hospital bed with the care/therapy modules may be used in hospitals, nursing homes, other care facilities, and in the home. The capability of providing a wide range of different care/therapy modules provides the user with a greater sense of security and stability in use of the module, thereby improving the user's sense of independence and self-sufficiency. In environments, such as the home, where a full bath facility may not be readily available, the flexibility of the hospital bed in combination with the different care/therapy modules permits a level of user care that would not otherwise be practical, thereby expanding the capability of home care.

While the invention as been set forth by a description of the preferred embodiments in considerable detail, it is not intended to restrict or in any way limit the claims to such detail. Additional advantages and modifications will readily appear to those who are skilled in the art. For example, the water care/therapy module may take other forms depending on the nature of care desired. For example, the water containment vessel may be made larger and elevated to permit a user to sit therein. With a bath-type module, the user seat would be perforated and a water collection vessel located thereunder. Alternatively, the water collection vessel may be larger to fully encompass the user and permit the user to shower therein. A water source for the shower may be provided by a self-contained water tank or a hose which is connectable to a faucet. The active leg exercise module is illustrated as providing a rotary motion exercise. Alternatively, the module may be designed to provide a back and forth reciprocating leg motion that simulates the climbing of stairs. The invention therefore in its broadest aspects is not limited to the specific details shown and described. Accordingly, departures may be made from such details without departing from the spirit and scope of the invention.

What is claimed is:

1. A bed facilitating comprehensive care of a user comprising:
   a base and frame assembly providing a foot end;
   an articulated support platform mounted on the base and frame assembly and selectively movable between a generally planar bed position and a chair position, the articulated support platform including
   a head panel moving to a raised position when moving the support platform to the chair position, and
   leg and foot panels moving relative to each other and the head panel to a position allowing the user to leave the bed through the foot end of the base and frame assembly when the support platform is in the chair position; and
   a commode removably coupled to the foot end of the base and frame assembly.

2. The bed of claim 1 wherein the base and frame assembly further comprise a plurality of support members for receiving and supporting frame members on the commode.

3. The bed of claim 2 wherein the frame moves in a generally vertical direction with respect to the base and the support members are connected to the frame to support and carry the commode in the generally vertical direction with the frame.

4. The bed of claim 3 wherein the commode includes a docking element and the support members include a latch connected to the frame for receiving the docking element.

5. The bed of claim 4 wherein the support members further comprise fixed surfaces located beneath different frame elements of the commode for supporting and lifting the commode with the frame.

6. The bed of claim 5 wherein the support member further comprise at least three fixed surfaces.

7. The bed of claim 6 wherein the support members further comprise four fixed surfaces located beneath different frame elements of the commode located proximate corners of the commode.

8. A bed facilitating comprehensive care of a user comprising:
   a base and frame assembly having a foot end;
   an articulated support platform mounted on the base and frame assembly and selectively movable between a generally planar bed position and a chair position, the articulated support platform including a head panel moving to a raised position when moving the support platform to the chair position, and leg and foot panels moving relative to each other and the head panel to a position allowing the user to leave the bed through the foot end of the base and frame assembly when the support platform is in the chair position;
   a care/therapeutic module removably coupled to the foot end of the base and frame assembly; and
   a latch connected to the base and frame assembly adjacent the foot end for receiving a member of the care/therapeutic module, the latch including a tube having an opening in a tube side wall proximate one end of the tube for receiving the member of the care/therapeutic module;
   a plunger slidably mounted within the tube, the plunger having a notch in one end for capturing the member of the care/therapeutic module; and
   a spring biasing the plunger toward the one end of the tube and pushing the member of the care/therapeutic module against a wall of the opening in the tube, thereby securing the member of the care/therapeutic module in a latched position with respect to the bed.

9. A bed having a generally planar bed position and convertible to a chair position, the bed comprising:
   a base and frame assembly having a foot end;
   an articulated support platform on the frame and including at least head, leg and foot panels, the head panel being mounted for pivotal movement relative to the frame for pivoting to a raised position and the leg and foot panel being mounted for pivotal movement relative to the frame for pivoting to a lowered position when converting from the bed position to the chair position so that a user's feet rest directly on the floor allowing the user to egress from the foot end of the base and frame assembly when in the chair position; and
   a care/therapeutic module removably coupled to the foot end of the base and frame assembly.

10. The bed of claim 9 further comprising a latch connected to the base and frame assembly adjacent the foot end for receiving a member of the care/therapeutic module.

* * * * *